United States Patent [19]

Czajka

[11] 4,219,020
[45] Aug. 26, 1980

[54] SCAVENGER VALVE ATTACHMENT FOR INHALATION SEDATION SYSTEM MASK

[75] Inventor: Ronald J. Czajka, Alden, N.Y.

[73] Assignee: Fraser Sweatman, Inc., Orchard Park, N.Y.

[21] Appl. No.: 932,118

[22] Filed: Aug. 9, 1978

[51] Int. Cl.³ .............................................. A61M 16/00
[52] U.S. Cl. ................................................. 128/207.13
[58] Field of Search ............... 128/188, 205, 195, 198, 128/206, 207, 208, 209, 210, 140 N, 139, 146.5, 146.4, 207.18, 910

[56] References Cited

U.S. PATENT DOCUMENTS

| 746,380 | 12/1903 | Richardson et al. | 128/205 |
| 2,016,212 | 10/1935 | O'Connell | 128/205 |
| 3,182,659 | 5/1965 | Blount | 128/205 |
| 3,721,239 | 3/1973 | Myers | 128/188 |
| 3,889,671 | 6/1975 | Baker | 128/140 N |
| 4,015,598 | 4/1977 | Brown | 128/188 |
| 4,151,843 | 5/1979 | Brekke et al. | 128/206 |

*Primary Examiner*—Henry J. Recla
*Attorney, Agent, or Firm*—Christel, Bean & Linihan

[57] ABSTRACT

A mask mounted scavenging valve attachment to scavenge gas emitting from an inhalation sedation system to the ambient environment.

4 Claims, 10 Drawing Figures

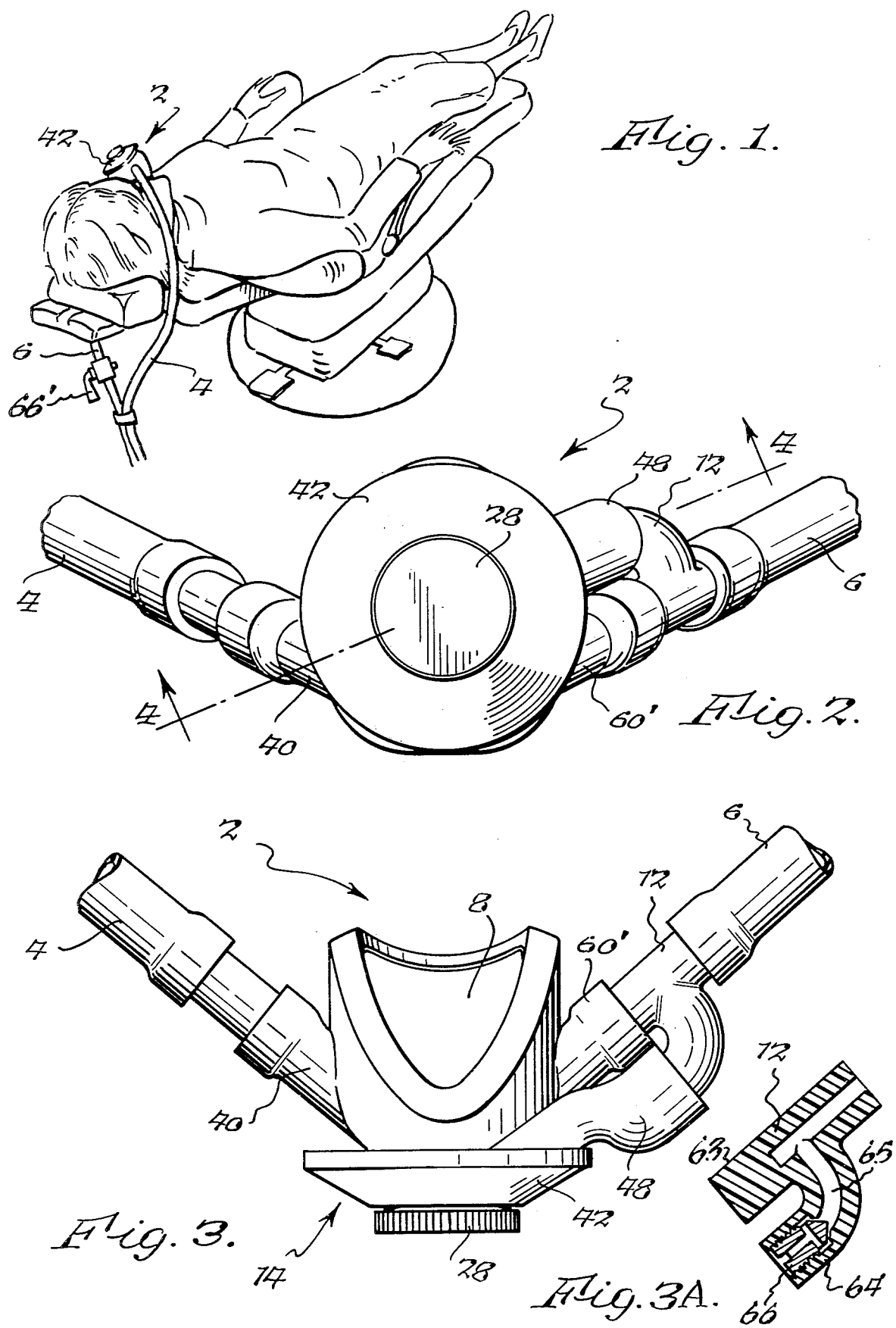

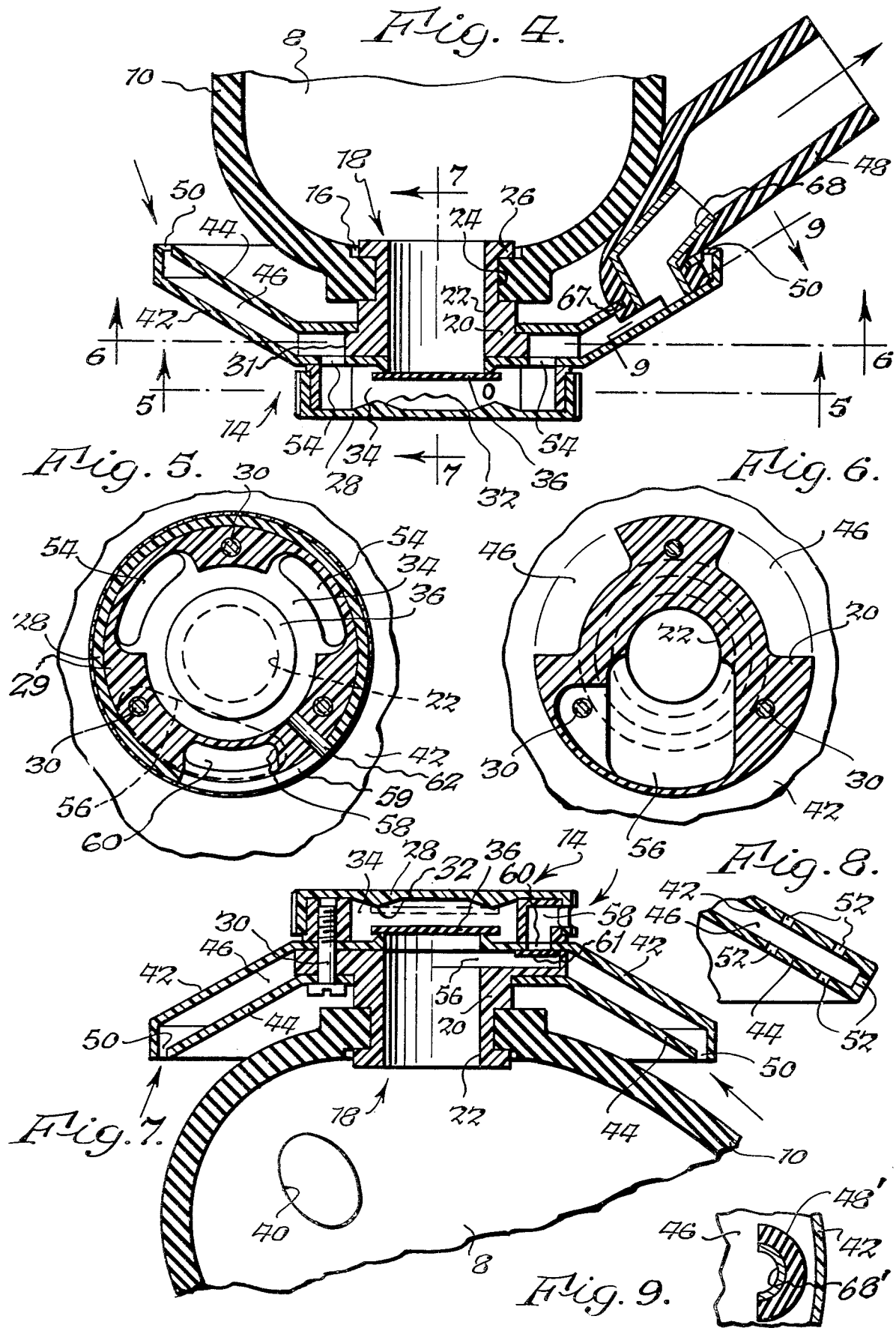

4,219,020

SCAVENGER VALVE ATTACHMENT FOR INHALATION SEDATION SYSTEM MASK

BACKGROUND

This invention is concerned with the scavenging of waste anesthetic gases emitted to the ambient environment during the administration of anesthesia or analgesia (inhalation sedation) by gas inhalation.

The administration of anesthetic or analgesic (inhalation sedation) gas to dental patients involves a mask (hood) placed over the nose of the patient and the introduction of a controlled amount of gas, through the mask, to the patient. Heretofore, such gas that either has leaked from the mask perimeter or was exhaled by the patient has been allowed to dissipate into the ambient environment. Recent concerns about the danger presented by this escaping gas in the environment of an operating room or dental office, particularly the side effects on personnel who are subject to this environment on a continual basis, have prompted increased attention and approaches to the elimination of such gas escape.

In one approach, as exemplified by U.S. Pat. No. 3,877,691 to Foster, an exhaust hood, connected to a vacuum system, overlies an extended area above the patient's face. The hood in a perforated hollow manifold and is transparent to permit the attending operator or surgeon to view the patient U.S. Pat. No. 3,271,239 to Meyers describes a suction manifold connected to the exhaust port or ports of an anesthesia system pop-off valve to capture the exhaust.

U.S. Pat. No. 4,015,598 to Brown discloses a double wall face mask being in essence, a mask over a mask. The inner mask defines a chamber over the patient's face communicating with a source of gas to be inhaled. The outer mask encloses and defines an exhaust chamber outside of the inner mask, the exhaust chamber communicating with a gas removal line. A check valve opens the facial chamber to the exhaust chamber during exhalation and the exhaust chamber is open to the surrounding atmosphere adjacent the face engaging perimeter of the inner mask to draw escaped gases from the surrounding atmosphere into the exhaust passage for disposal.

SUMMARY OF THE INVENTION

It is an object of this invention to provide a scavenging attachment for an inhalation face mask which is light in weight, small in size, convenient to use and which can be fitted to existing masks of various sizes and configurations.

In one form, the scavenging attachment of this invention is mounted on a face mask in place of a conventional exhalation valve. An exhalation aperture leads, through a floating disc check valve, to a vacuum chamber which extends in a generally concave inverted saucer configuration over and around the mask. The vacuum chamber communicates with the surrounding atmosphere by means of an annular aperture, or one or more smaller apertures, in order to scavenge from the atmosphere adjacent to the patient's face any gas escaping from the periphery of the mask.

For a better understanding of this invention, reference is made to the following detailed description of an exemplary embodiment, given in connection with the accompanying drawing.

DRAWING

FIG. 1 is a perspective view of a patient reclining in a dental chair and fitted with a sedation mask equipped with a scavenger assembly of this invention.

FIG. 2 is an end view of the scavenger valve, mask and associated conduits of FIG. 1.

FIG. 3 is a top view of the mask and scavenging attachment.

FIG. 3A is a longitudinal sectional view of an exhaust line fitting.

FIG. 4 is an enlarged sectional view of the mask and scavenging assembly taken along the line 4—4 of FIG. 2.

FIG. 5 is a sectional view of the scavenging attachment taken along the line 5—5 of FIG. 4.

FIG. 6 is a sectional view of the scavenging attachment taken along the line 6—6 of FIG. 4.

FIG. 7 is a sectional view of the mask and scavenging attachment taken along the line 7—7 of FIG. 4.

FIG. 8 is a fragmentary sectional view of a modified scavenger manifold of this invention.

FIG. 9 is a fragmentary sectional view taken about along the line 9—9 of FIG. 4.

DESCRIPTION

Referring now to FIG. 1, a patient is shown reclining in a dental chair. A gas delivery mask is generally indicated at 2 overlying the nose of the patient. Mask 2 can be of known design, and is of a flexible rubber or plastic material molded to fit over the nose bridge and adjacent facial area to define with the face an enclosed mask chamber. A pair of gas lines 4 and 6 connect to the mask 2. Conventionally, lines 4 and 6 are both supply lines for delivery of analgesic or anesthetic gas to the mask chamber 8 and to the patient. In the present system, however, only line 4 is the gas supply line leading into chamber 8. Line 6 is a gas exhaust or vacuum line and leads to a remotely located gas collection and disposal system, not shown, but of a type which is common in hospitals and dental offices. The scavenging attachment of this invention is mounted on mask 2 and provides for inhalation of the desired gas, such as a nitrous oxide and oxygen mixture, through the supply line 4 and chamber 8 to the patient, and exhalation from the patient through chamber 8 and the exhaust line 6 to the vacuum system for disposal.

FIGS. 2 and 3 show the adaptation or retrofitting of a known mask with the scavenger of the present invention. Mask 2 includes a mask body member 10 including a first inlet passage 40 and a second inlet passage 60 which connect respectively to the lines 4 and 6. While in the prior art mask passage 60 openly connects chamber 8 with a gas line 6, in the present case passage 60 is blanked off and by-passed by a tee member 12 by which exhaust line 6 is connected in communication with the scavenging attachment, as will be described. Tee member 12 is dead ended where it connects with passage 60. A combination exhalation disc valve and scavenging system of this invention generally indicated at 14, is mounted on the front of mask body 10.

Referring now to FIG. 4, the mask 2 is shown in cross-section in which the mask body 10 defines an exhalation aperture 16 in its front into which the exhalation valve—scavenging combination 14 is inserted. The exhalation valve 18 includes a generally cylindrical valve body 20 defining a cylindrical exhaust passage 22 therethrough. Valve body 20 preferably is of a rigid plastic material and is suitably recessed at 24 and flanged at 26 so as to seat firmly but removably in the aperture 16 of the flexible mask body 10. Valve body 20 carries the scavenging assembly, and releasably fits in the mask aperture 16 in place of a conventional exhalation valve body without such a scavenging arrangement.

A valve cover 28 in the form of a cup or hollow cylinder closed at one end is open to the exhaust passage 22 and is captively rotatable on an annular mounting member 29 which is fastened to valve body 20 by suitable fasteners 30 (FIG. 7). Valve cover 28 and mounting member 29 define an exhaust chamber 34, of a diameter greater than that of the exhaust passage 22. A floating valve disc 36, greater in diameter than the passage 22, is axially movable in chamber 34 between the seated or closed position of FIGS. 4 and 7 and an unseated or open position represented in phantom in FIG. 7. Valve disc 36 is prevented from inadvertently adhering to cover 28 in the open position by several pointed projections 32 which form a part of cover 28, and is of a size relative to passage 22 and the confining side wall of member 29 such that it always closes passage 22 when in its closed position. Valve 36 moves to its closed position in response to an inhalation effort by the user.

An outer frusto-conical shroud 42 and an inner frusto-conical shroud 44, axially spaced from the outer shroud 42, together define a frusto-conical scavenging chamber 46. Shrouds 42, 44 are secured to valve body 20 by and between mounting member 29 and fasteners 30, the laterally projecting outer flange 31 of body 20 spacing apart members 42, 44. A vacuum passage 48 leads from the scavenging chamber 46 to tee member 12 and gas exhaust line 6, thus finally to vacuum. In the preferred embodiment of this invention, shrouds 42, 44 do not join at their outer periphery but define a peripheral annual scavenging passage 50 by which the scavenging chamber 46 is in communication with the atmosphere surrounding the patient's face. Alternatively, the desired results may be achieved by having outer and inner shrouds 42, 44 of a single or integral member with a plurality of scavenging passages 52 formed through the shrouds to effect communication of scavenging chamber 46 with ambient atmosphere, as shown in FIG. 8. If desired, both types of scavenging passages can be used.

Exhaust passage 22 and exhaust chamber 34 of the exhalation valve 18 communicate with scavenging chamber 46, and thus with the vacuum system, through a plurality of valve ports 54, shown in FIGS. 4 and 5.

Sometimes ambient air dilution is desired. Valve cover 28 is rotatably mounted on member 29 for selective opening and closing of an ambient air inlet. Valve body 20 has internal passage 56 extending radially through a portion of its wall, formed by a recess in the outer end of body 20. Similarly, cover mounting member 29 includes a passage 58 of even more limited lateral extent, extending radially from the exterior thereof and inwardly through an opening 60 in shroud 42 at a right angle to communicate with internal passage 56. Valve cover 28 has a slot type opening 59 through its depending skirt and is rotatable between a position aligning openings 58 and 59 (FIG. 7) and a position closing opening 58 from the ambient atmosphere. The purpose of passages 56 and 58 is to supplement the analgesic gas supply to the patient with ambient air in appropriate circumstances. A pin 62 carried by member 29 engages opposite ends of slot 59 to limit relative movement and define fully open and fully closed positions. A normally closed flapper valve 61 permits inhalation of ambient air when passages 58, 59 are aligned and open, while preventing the escape of exhaled gas therethrough from the mask chamber. Flapper valve 61 is sufficiently shape sustaining to remain normally closed, while opening in response to the added effect of an inhalation effort.

Connecting member 12 has a plug end 63 (FIG. 3A) received in mask inlet 60' to plug the same, the branch 64 of member 12 being received in exhaust passage 48 and having a passage 65 placing the scavenging shroud in communication with the suction source. The outer end of passage 65 is enlarged to provide an annular shoulder and a needle type throttling valve 66 having a passage therethrough is threaded into the enlarged outer end of passage 65 to throttle the flow of the suction source to provide only what is needed for effective scavenging, thereby avoiding unnecessary suction flow and needless energy waste. A shut-off valve 66' is provided in suction line 6 (FIG. 1) permitting the suction source to be closed off when the mask is not in use.

Suction passage 48 is peripherally grooved near its inner end 67 for attachment to scavenger housing wall 44, as shown in FIG. 4. A rigid elbow 68 fits within conduit 48 and with the inner end 67 of conduit 48 extends into the scavenging chamber 46 to the opposite wall 42. Portions of members 68, 48 between walls 42, 46 are removed to provide a passage opening facing the center of the scavenger housing while leaving barrier portions 68', 48' (FIG. 9) which space apart walls 42 and 44 and act as a barrier against dissipation of the suction effect by short circuiting directly from passage 48 to opening 50. Elbow 68 supports conduit 48 against collapse adjacent its point of attachment to the scavenger housing.

In operation, with mask 2 in place over a patient's nose, the patient inhales gas from supply line 4 through inlet passage 40 and mask chamber 8 into the patient's respiratory system. During inhalation, the floating valve disc 36 of exhalation valve 18 is in closed position as shown in FIG. 4. During exhalation, the floating valve disc 36 is unseated and exhalation from the patient flows through mask chamber 8, exhaust passage 22, past the now open valve disc 36 into exhaust chamber 34, through valve ports 54 to scavenging chamber 46, vacuum passage 48, and finally through exhaust line 6 to the vacuum source. If auxiliary air inlet 56, 58 is open, by hand rotation of valve cover 28, there is, in addition, a communication between patient and ambient air during inhalation but not exhalation. The operation of the system to scavenge escaping gas is not significantly affected by the air inlet.

At all times, scavenging chamber 46 is in communication with the vacuum system and is aspirating or scavenging air and gas through scavenging passage 50 (or 52 in the modified embodiment). In short, the passage 50 or 52 are suction passages, near the perimeter of contact betweem mask and face where any gas leakage occurs, to draw away any such gas and prevent its further escape into the room atmosphere.

The scavenging system of this invention, as will be appreciated especially from FIGS. 4 or 7, is simply attached to the mask body 10 by insertion of the body 18 into the mask aperture 16.

The scavenging valve attachment of this invention will fit onto any of several sizes of existing masks whereby it is not necessary to mold a special scavenging mask for each size and existing masks can be retrofitted by removing the conventional exhaust valve to atmosphere and inserting the scavenging valve attachment in its place. The attachment is positioned immediately adjacent the area to be scavenged, and is positioned out of the way of the doctor and any attendants.

The foregoing description and summary of this invention are given only by way of illustration and not of limitation.

What is claimed is:

1. A mask assembly for administering a gas to be inhaled by an individual including,
   a mask body to fit over the nose of said individual, and against the surrounding facial area of said individual,
   said mask body terminating in a peripheral surface contoured to fit against the facial area of said individual and when so positioned defining therewith a mask chamber,
   said mask body including an inlet port adapted to be operatively connected to a source of gas to be administered to said individual thereby to direct said gas to said mask chamber,
   valve means including a valve body member disposed through said mask body in an area of said mask body remote from said contoured peripheral surface, said valve body member including an exhalation valve member movable between a first seated closed position during inhalation of said individual and a second open position during exhalation of said individual,
   said valve body member including a first exhaust chamber formed about said exhalation valve member to receive exhalation gas of said individual flowing through said exhalation valve member and a second annular exhaust chamber formed of a pair of substantially frusto-conically shaped members radiating outwardly from said valve body member and spaced from each other to define said second annular exhaust chamber,
   means affording fluid communication between said first and second exhaust chambers and an outlet port adapted to be connected to a vacuum source in one of said exhaust chambers thereby to provide a source of vacuum to each said first and second exhaust chambers to exhaust gas exhaled by said individual,
   said pair of radiating members defining an area at their terminii, said area being disposed circumferentially and outwardly of said mask body and being located distantly from said periphery surface and the facial area of the said individual when the mask is in use and being spaced from said inlet port, and
   said pair of radiating members having inlet means to said annular exhaust chamber near the outer edge surface of said annular exhaust chamber thereby to establish a suction effect about the whole exterior of said mask body when said mask body is connected to said vacuum source.

2. A mask assembly as defined in claim 1 in which said exhalation valve member is a floating disc freely movable between said first and second positions.

3. A mask assembly as defined in claim 1 wherein said mask assembly further includes ambient air inlet means into said mask chamber controllable between an open position to allow ambient air to flow into said mask chamber to a closed position precluding the flow of ambient air into said mask chamber.

4. A mask assembly as defined in claim 3 wherein said ambient air inlet means includes means to preclude the escape of exhaled gas from said mask chamber back through said ambient air inlet means.

* * * * *

UNITED STATES PATENT AND TRADEMARK OFFICE
CERTIFICATE OF CORRECTION

PATENT NO. : 4,219,020
DATED : August 26, 1980
INVENTOR(S) : Ronald J. Czajka

It is certified that error appears in the above–identified patent and that said Letters Patent are hereby corrected as shown below:

Claim 1, column 6, line 14, "periphery" should be

--peripheral--.

Signed and Sealed this

Third Day of February 1981

[SEAL]

Attest:

RENE D. TEGTMEYER

Attesting Officer     Acting Commissioner of Patents and Trademarks